United States Patent [19]

Kamakura et al.

[11] Patent Number: 5,494,608
[45] Date of Patent: Feb. 27, 1996

[54] POWDERY MOLYBDENUM OXYSULFIDE DITHIOCARBAMATE COMPOSITION, A PROCESS FOR PRODUCING SAME, AND A GREASE COMPOSITION CONTAINING THE COMPOSITION

[75] Inventors: Tamiji Kamakura; Noriyoshi Tanaka; Aritoshi Fukushima; Yukio Tatsumi; Kazuhisa Morita, all of Tokyo, Japan

[73] Assignee: Asahi Denka Kogyo K.K., Toyko, Japan

[21] Appl. No.: 284,128

[22] Filed: Aug. 2, 1994

[30] Foreign Application Priority Data

Aug. 13, 1993 [JP] Japan .................... 5-201498

[51] Int. Cl.$^6$ .................... C10M 115/00; C07F 1/00
[52] U.S. Cl. .................... 252/42.7; 556/38
[58] Field of Search .................... 252/42.7; 556/38

[56] References Cited

U.S. PATENT DOCUMENTS

| | | | |
|---|---|---|---|
| 3,356,702 | 12/1967 | Farmer et al. | 556/38 |
| 3,840,463 | 10/1974 | Froeschmann et al. | 252/42.7 |
| 4,098,705 | 7/1978 | Sakurai et al. | 556/38 |
| 4,315,826 | 2/1982 | Schlicht et al. | 556/38 |
| 4,683,316 | 7/1987 | Singhal | 556/38 |
| 5,281,347 | 1/1994 | Igarashi et al. | 252/42.7 |

FOREIGN PATENT DOCUMENTS

| | | | |
|---|---|---|---|
| 1559588 | 3/1969 | France. | |
| 2320305 | 3/1977 | France. | |
| 80825 | 7/1976 | Japan | 556/38 |
| 4182494 | 6/1992 | Japan | 556/38 |

*Primary Examiner*—Ellen M. McAvoy
*Attorney, Agent, or Firm*—Oblon, Spivak, McClelland, Maier, & Neustadt

[57] ABSTRACT

A powdery molybdenum oxysulfide dithiocarbamate composition which comprises a compound represented by the following general formula (1):

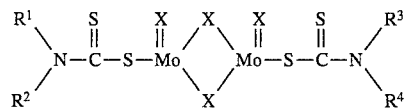

wherein $R^1$, $R^2$, $R^3$ and $R^4$ are independent hydrocarbyl groups and may be the same or different groups, and the total number of carbon atoms contained in $R^1$ to $R^4$ is 4 to 36; and wherein X is sulfur or oxygen and the composition of the total of all Xs is given as $S_m O_n$ in which n and m satisfy the ranges of $1.7 \leq m \leq 3.5$ and $0.5 \leq n \leq 2.3$, respectively, and in which the constituent particles have diameters of not larger than 50 μm. The present invention also relates to a process for production of the composition and a grease composition containing the same.

13 Claims, No Drawings

POWDERY MOLYBDENUM OXYSULFIDE DITHIOCARBAMATE COMPOSITION, A PROCESS FOR PRODUCING SAME, AND A GREASE COMPOSITION CONTAINING THE COMPOSITION

BACKGROUND OF THE INVENTION

1. Field of the Invention

The present invention relates to a powdery molybdenum oxysulfide dithiocarbamate composition, a process for producing same and a grease composition containing the composition. More specifically, the present invention relates to a powdery molybdenum oxysulfide dithiocarbamate composition which exhibits low corrosive action and has excellent lubricating properties, a process for producing it and a grease composition containing the composition.

2. Description of the Related Art

Heretofore, adding molybdenum oxysulfide dithiocarbamate to grease has been tried in order to improve extreme pressure properties, friction modifier properties and anti-wear properties of grease. Various methods for producing such molybdenum oxysulfide dithiocarbamate have been disclosed. For example, Japanese Patent Publication No.45-24562 discloses a method by which a compound having the general formula:

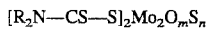

(wherein m+n=4, m=2.35–3, n=1.65–1, and R is a hydrocarbyl group having 1 to 24 carbon atoms) can be produced by reacting together a secondary amine, carbon disulfide and molybdenum trioxide.

Japanese Patent Laid-Open No.48-56202 discloses a method in which a compound represented by the following general formula:

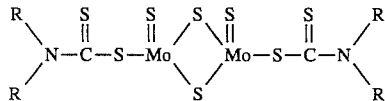

(wherein R is an alkyl group) can be produced by reacting the product given by the method of Japanese Patent Publication No.45-24562 described above with phosphorus pentasulfide, In addition, Japanese Patent Laid-Open Nos. 52-19629 and 52-106824 disclose methods by which a compound represented by the following general formula:

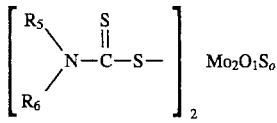

(wherein $R_5$ and $R_6$ are independently hydrocarbyl groups having 1 to 24 carbon atoms, l is a number from 0.5 to 2.3, o is a number from 3.5 to 1.7 and l+o=4) can be produced by reacting carbon disulfide with a secondary amine in an aqueous solution or suspension containing molybdenum trioxide or an alkali metal salt or an ammonium salt of molybdic acid and an alkali hydrogensulfide or an alkali sulfide in a molar ratio of 1:0.05–4.

However, the compound of Japanese Patent Publication No. 45-24562 above is inferior in heat resistance and, in the grease preparation process, may cause a color change in the resulting grease. On the other hand, the compound described in Japanese Patent Laid-Open No. 48-56202 exhibits corrosive action against copper plates, thus the use of the compound has been limited. The compound described in Japanese Patent Laid-Open Nos.52-19629 and 52-106824 also still has room for improvement in terms of lubricating properties and corrosive properties. That is, when the powdery molybdenum oxysulfide dithiocarbamate is added to the grease to prepare a grease composition, its physical properties such as particle size have been neglected. As a result, the grease composition produced is not imparted with sufficient lubricating properties, and furthermore may cause slight vibrations.

SUMMARY OF THE INVENTION

An object of the present invention is to provide a powdery molybdenum oxysulfide dithiocarbamate composition which, when used for a grease composition, exhibits excellent wear and friction properties and, therefore, exhibits excellent lubricating properties, as well as decreased corrosive action.

Another object of the present invention is to provide a process for effective production of the powdery molybdenum oxysulfide dithiocarbamate composition described above.

A further object of the present invention is to provide a grease composition which exhibits excellent wear and friction properties and, therefore, exhibits excellent lubricity properties, as well as less corrosive action.

DETAILED DESCRIPTION OF THE INVENTION

The present inventors have carried out extensive research on various kinds of purified molybdenum oxysulfide dithiocarbamate from the viewpoint of corrosive action and lubricating properties. As a result, they have found a component effective for use as an additive for a grease composition and a process for producing the component, thereby attaining the present invention.

That is, according to the present invention, a powdery molybdenum oxysulfide dithiocarbamate composition can be provided which comprises a compound represented by the following general formula (1):

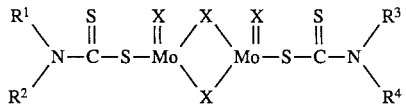

(wherein $R^1$, $R^2$, $R^3$ and $R^4$ are independent hydrocarbyl groups and may be the same or different groups, and the total number of carbon atoms contained in $R^1$ to $R^4$ is 4 to 36; and wherein X is sulfur or oxygen and the composition of the total of all Xs is given as $S_mO_n$ in which m and n satisfy the ranges of $1.7 \leq m \leq 3.5$ and $0.5 \leq n \leq 2.3$, respectively), and in which constituent particles have diameters of not larger than 50 μm.

The powdery molybdenum oxysulfide dithiocarbamate composition according to the present invention can be produced by a process characterized in that:

(A) an aqueous solution or suspension prepared by reacting (a) molybdenum trioxide or an alkali metal salt or ammonium salt of molybdic acid with (b) alkali hydrogensulfide or alkali sulfide in a molar ratio of (a):(b)=1:1 to 1:2, (B) carbon disulfide, (C) secondary amine and
(D) mineral acid
are reacted together, wherein the molar ratio of (A), (B) and (C) is (A):(B):(C)=1:0.9–2:0.9–2 and the amount of (D) to be added is within the range satisfying the following equation (1):

$$1-[(R'/4)+1]\times 1/10 \leq d \leq 1$$

[wherein R' is the total number of carbon atoms contained in $R^1$, $R^2$, $R^3$ and $R^4$ in formula (1) and d is the equivalent number of the alkali in the mineral acid as opposed to the alkali present in (A)] when the alkali equivalent in (A) is defined as 1, whereby a solid reaction product is obtained;

the resulting reaction product is slurryed with an organic solvent; and then the resulting slurry is washed, dried and powdered.

The grease composition of the present invention is characterized by containing 0.1 to 10 parts by weight of a powdery molybdenum oxysulfide dithiocarbamate composition which comprises a compound represented by the following general formula (1):

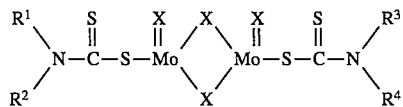

(wherein $R^1$, $R^2$, $R^3$, $R^4$, X, m and n are the same as defined above), and of in which constituent particles have diameters of not larger than 50 μm, based on 100 parts by weight of a base grease.

In the compound of formula (1) to be used in the present invention, the hydrocarbyl groups represented by $R^1$, $R^2$, $R^3$ and $R^4$ may be saturated or contain unsaturated bond(s), may be straight chains, branched chains or cyclic chains or any combined form thereof, and may be the same or different. However, the total number of carbon atoms contained in $R^1$, $R^2$, $R^3$ and $R^4$ should be 4 to 36, preferably 4 to 32, and more preferably 8 to 32. When the total number is greater than the range above, the compound exhibits a lower melting point and therefore may become viscous at ordinary temperatures, resulting in poor handling, which is not desirable.

As such hydrocarbyl groups, aliphatic, aromatic and aromatic-aliphatic groups can be employed. Typical examples of such hydrocarbyl groups include alkyl groups such as methyl, ethyl, propyl, isopropyl, butyl, isobutyl, hexyl, octyl, 2-ethylhexyl, nonyl, decyl, lauryl, tridecyl, isotridecyl, myristyl, palmityl and stearyl; alkenyl groups such as propenyl, butenyl, isobutenyl, pentenyl, 2-ethylhexenyl, octenyl, oleyl and palmitoleyl; cycloalkyl groups such as cyclopentyl, cyclohexyl, methylcyclohexyl and ethylcyclopentyl; aryl groups such as phenyl, naphthyl and alkyl substituent phenyl; aralkyl groups such as benzyl and phenethyl; and so on. Among these, preferably used are ethyl, propyl, isopropyl, butyl, isobutyl, pentyl, hexyl, heptyl, octyl, 2-ethylhexyl and the like.

In the compound of formula (1), X is sulfur or oxygen, and the composition of the total of all Xs is given as $S_mO_n$ wherein m satisfies the range of $1.7 \leq m \leq 3.5$ and preferably $1.8 \leq m \leq 3.0$ and n satisfies the range of $0.5 \leq n \leq 2.3$ and preferably $1.0 \leq n \leq 2.2$. When m is higher than the above range (i.e. n is lower than the above range), the compound exhibits undesirable corrosive properties. On the other hand, when m is lower than the above range (i.e n is higher than the range above), the compound exhibits poor lubricating properties. For these reasons, values of m and n which lie outside of the above range are not preferable.

In the molybdenum oxysulfide dithiocarbamate composition of the present invention which comprises a compound represented by formula (1), the constituent particles, i.e. the molybdenum oxysulfide dithiocarbamate particles, have diameters of not larger than 50 μm. Preferably, the composition contains particles of molybdenum oxysulfide dithiocarbamate of not smaller than 40 to not larger than 50 μm in diameter in an amount of not more than 5% by weight and particles of smaller than 40 μm in diameter in an amount of not less than 95% by weight, based on the total weight of the particles. Furthermore, in the molybdenum oxysulfide dithiocarbamate composition, it is most preferable that the average diameter of all of the particles is not larger than 20 μm in addition to the conditions described above.

An increase in particle diameter of the powdery molybdenum oxysulfide dithiocarbamate may cause not only a decrease in dispersibility in grease but also less effective lubricating properties thereof. For these reasons, the molybdenum oxysulfide dithiocarbamate particles which compose the powdery molybdenum oxysulfide dithiocarbamate composition of the present invention should have particle diameters of not larger than 50 μm.

Such powdery molybdenum oxysulfide dithiocarbamate compositions may be produced by synthesizing a molybdenum oxysulfide dithiocarbamate composition according to a conventional process known and then sieving the resultant composition. However, the composition can be prepared more effectively according to the process described below.

That is, the powdery molybdenum oxysulfide dithiocarbamate composition can be produced according to a process in which:

(A) an aqueous solution or suspension prepared by reacting (a) molybdenum trioxide or an alkali metal salt or ammonium salt of molybdic acid with (b) alkali hydrogensulfide or alkali sulfide in a molar ratio of (a):(b)=1:1 to 1:2, (B) carbon disulfide, (C) secondary amine and (D) mineral acid are reacted together, wherein the reaction molar ratio of (A), (B) and (C) is (A):(B):(C)=1:0.9–2:0.9–2 and the amount of (D) to be added is within the range satisfying the following equation (1):

$$1-[(R'/4)+1]\times 1/10 \leq d \leq 1$$

[wherein R' is the total number of carbon atoms contained in $R^1$, $R^2$, $R^3$ and $R^4$ in the formula (1) and d is the equivalent number of the mineral acid against the alkali present in (A)] when the alkali equivalent in (A) is defined as 1, to give a solid reaction product;

the resulting reaction product is slurryed with an organic solvent; and then the resulting slurry is washed, dried and powdered.

As the alkali metal salt and ammonium salt of the molybdic acid to be used as component (a) in the process above, conventionally employed are sodium molybdate, potassium molybdate, ammonium molybdate and the like.

As the alkali hydrogensulfide to be used as component (b), sodium hydrogensulfide, potassium hydrogensulfide and the like can be employed in flake form or as an aqueous solution. However, from the viewpoint of reactivity with solid molybdenum trioxide, an aqueous alkali hydrogensulfide solution is preferable.

As the alkali sulfides to be used as component (b), conventionally employed are sodium sulfide, potassium sulfide, ammonium sulfide and the like. In addition, an aqueous alkali sulfide solution can also be employed which is prepared by introducing a sulfurizing gas into an aqueous alkali hydroxide solution. However, from the viewpoint of corrosive action of the resulting product, it is preferable to use a solid such as sodium sulfide, potassium sulfide, ammonium sulfide or the like.

In the process for preparation of the molybdenum oxysulfide dithiocarbamate composition of the present invention, (a) molybdenum trioxide or an alkali metal salt or ammonium salt of molybdic acid [hereinafter, simply referred to as "(a) molybdenum trioxide etc."] must be reacted at least partially, preferably more than 50 mole %, and more preferably more than 80 mole %, with (b) alkali hydrogensulfide or alkali sulfide [hereinafter, simply referred to as "(b) alkali hydrogensulfide etc."], prior to the reaction with (C) secondary amine, (B) carbon disulfide and (D) mineral acid. If component (a) is not at all initially reacted with component (b), a large amount of by-products may indesirably produced in the subsequent reaction with the components (B), (C) and (D). The reaction between components (a) and (b) can be almost entirely completed within 30 to 60 minutes by stirring at from an ordinary temperature to 60° C.

The molar ratio between (a) molybdenum trioxide etc. and (b) alkali hydrogensulfide etc. is a factor for determination of the composition of Xs in formula (1). The ratio should be 1.0 to 2.0 moles, preferably 1.2 to 1.9 moles of (b) alkali hydrogensulfide etc. based on 1 mole of (a) molybdenum trioxide etc. A smaller ratio of (b) alkali hydrogensulfide etc. than the above range may cause the production of a large amount of isomers as Xs in formula (1) which contain a great deal of oxygen, thus resulting in poor lubricating properties of the composition, which is not preferable. On the other hand, a larger ratio of (b) alkali hydrogensulfide etc. than the above range may cause the production of a large amount of isomers as Xs in the general formula (1) which contain a great deal of sulfur, thus resulting in higher corrosive action of the composition, which is also not preferable.

In the present invention, (a) molybdenum trioxide etc. and (b) alkali hydrogensulfide etc. may be used in a solid form, aqueous solution or suspension or the like, so long as the reaction system contains water at least at the point when the reaction between (a) and (b) is carried out. For example, at least either of the components (a) or (b) is mixed in as an aqueous solution or suspension with the other, or both of the components are mixed in as solids and then water is added to the solid mixture to give an aqueous mixture solution or suspension to be then reacted. The reactant thus prepared is "(A) an aqueous solution or suspension".

Also, in the step of preparing (A) an aqueous solution or suspension by reacting (a) molybdenum trioxide etc. with (b) alkali hydrogensulfide etc., an organic solvent may be added to the reaction system before and/or during and/or after the reaction in a desired amount within a range which does not inhibit the reaction. As the thus used organic solvent, the same as those used in the slurrying step described below can be employed. However, this organic solvent is separate from that used in the slurrying step, and therefore is not taken into account as part of the total organic solvent used in slurrying step below.

In the secondary amine (C) to be used, the hydrocarbyl substituent groups may be saturated or contain unsaturated bond(s), and may be straight chains, branched chains or cyclic chains or any combined form thereof, and may be the same or different. As such hydrocarbyl groups, aliphatic, aromatic and aromatic-aliphatic hydrocarbyl groups can be employed. Typical examples of such hydrocarbyl groups include alkyl groups such as methyl, ethyl, propyl, isopropyl, butyl, isobutyl, hexyl, octyl, 2-ethylhexyl, nonyl, decyl, lauryl, tridecyl, isotridecyl, myristyl, palmityl and stearyl; alkenyl groups such as propenyl, butenyl, isobutenyl, pentenyl, 2-ethylhexenyl, octenyl, oleyl and palmitoyl; cycloalkyl groups such as cyclopentyl, cyclohexyl, methylcyclohexyl and ethylcyclopentyl; aryl groups such as phenyl, naphthyl and alkyl-substituted phenyl; aralkyl groups such as benzyl and phenethyl; and so on. It is preferable to use one or more types of secondary amines substituted with one or more of the hydrocarbyl groups selected from ethyl, propyl, isopropyl, butyl, isobutyl, pentyl, hexyl, heptyl, octyl, 2-ethylhexyl and so on.

As the mineral acid (D) to be used in the process described above, one or more kinds of acids other than organic acids selected from monobasic acids (e.g. hydrochloric acid, nitric acid, etc.), dibasic acids (e.g. sulfuric acid, etc.) and tribasic acid (e.g. phosphoric acid, etc.) and partially neutralized acids thereof may be employed.

In the process described above, any reaction order for components (A), (B), (C) and (D) can be employed. However, from the viewpoint of not producing by-products, the reaction order in which the components (B) and (C) are added simultaneously is preferable. More specifically, the reaction order preferably employed is one in which the components (B) and (C) are initially added to component (A) simultaneously and then component (D) is added to the resultant mixture, or in which the component (D) is initially added to the component (A) and then the components (B) and (C) are added to the resultant mixture simultaneously.

The molar ratio of (A) an aqueous molybdenum solution etc.: (C) a secondary amine: (B) carbon disulfide influences the production of by-products of the intended product. Therefore, the molar ratio of (A):(C):(B) to be employed is 1:0.9–2:0.9–2, and preferably 1:1–1.5:1–1.5, by which the by-product content in the product decreases.

The amount of the component (D) to be added should satisfy the following equation (1):

$$1-[(R'/4)+1 \times 1/10 \leq d \leq 1$$

(wherein R' and d have the same meaning as defined above) when the equivalent of alkali present in (A) is defined as 1. The amount of the component (D) to be added is closely related to the yield of by-products and the intended product. An increase in the amount of (D) added leads to a higher yield of by-products, whereas a decrease in the amount of (D) added leads to the lower yield of the intended product.

In the process described above, the components (A), (B), (C) and (D) can sufficiently react with one another at approximately room temperature. However, the reaction temperature to be employed is preferably from 40° to 140° C. and is especially preferable from 60° to 110° C. The reaction time is from about 2 to 15 hours.

According to the process described above, a solid reaction product in a water suspension can be obtained. By washing, purifying, powdering and finally sieving the solid reaction product, the powdery molybdenum oxysulfide dithiocarbamate composition of the present invention can be obtained. However, this process has the disadvantages that it is hard to powder the product well because of its solid form, and also that the trace amount of metal content and by-products contained in the resulting solid reaction product can not be readily removed.

Accordingly, in order to effectively produce the powdery molybdenum oxysulfide dithiocarbamate composition of the present invention which comprises the compound represented by formula (1) above, the solid reaction product obtained by the reaction described above is slurryed with an organic solvent once before it is subjected to washing and powdering steps. Due to incorporating the slurrying step into the process, the metal contents and by-products contained in the reaction product are easily removed by washing and, furthermore, a high yield of a powdery molybdenum oxysulfide dithiocarbamate composition having a small particle size can be readily obtained without a sieving step.

As the organic solvent to be used for slurrying in the process of the present invention, any organic solvent can be employed so long as it is a volatile organic compound such as an aliphatic, aromatic and aliphatic-aromatic compound. Examples of such organic compounds include alkanes such as pentane, hexane, cyclohexane and cyclopentane; alcohols such as methanol, ethanol, 2-propanol, propanol, butanol and amyl alcohol; alkyl ethers such as diethyl ether and ethyl-propyl ether; aromatic compounds such as benzene, toluene and xylene; and other conventional organic solvents such as tetrahydrofuran, pyridine, carbon tetrachloride, chloroform and dimethyl sulfoxide. Among these, from the viewpoint of dispersibility of the reaction product, alcohols such as methanol, ethanol and 2-propanol and aromatic compounds such as benzene, toluene and xylene are preferable.

Any amount of such an organic solvent can be employed so long as the reaction product can be slurryed, for example within a range of from 0.1 to 10 times by weight, preferably from 0.3 to 3 times by weight, the weight of the molybdenum trioxide (a) charged. An organic solvent in an amount smaller than the above range can not disperse the reaction product sufficiently; also the organic solvent in an amount larger than the above range can not greatly improve the dispersion effect. In the contrary, it makes the removal step for the solvent troublesome: both results being not preferable.

The powdery molybdenum oxysulfide dithiocarbamate composition of the present invention, which comprises the compound represented by formula (1), can be produced by slurrying the reaction product as described above and, if required, then washing the resulting slurry with water or a suitable organic solvent, and finally drying and powdering.

The grease composition of the present invention can be obtained by using the powdery molybdenum oxysulfide dithiocarbamate composition produced above, wherein the composition is added to a base grease in an amount of 0.1 to 10 parts by weight, preferably 0.5 to 5 parts by weight, based on 100 parts by weight of the base grease. The grease composition thus obtained exhibits less corrosive action and has excellent lubricating properties.

If the content of the molybdenum oxysulfide dithiocarbamate composition is less than the above described range, sufficient lubricating properties can not be imparted. On the other hand, even if the content of the composition is higher than the above range, the intended effects can not be further improved. For these reasons, too low or too high a content of the composition is not appropriate industrially.

The base grease to be used in the grease composition is, for example, a metallic soap grease, a metallic soap complex grease, an urea-based grease or a grease using organically treated clay (e.g. bentone grease), in which a mineral oil and/or a synthetic oil is used.

The grease composition of the present invention may be incorporated with an extreme pressure agent such as zinc dithiophosphate, a sulfur-phosphorous compound or molybdenum dithiophosphate, etc. and a solid lubricant such as molybdenum disulfide, graphite and ethylene tetrafluoride etc.. In addition, if necessary, other conventional components may also be added to the grease composition as additives for grease, such as a rust preventative (e.g. N-N-trimethylenediaminedioleate, sorbitan monooleate, etc.), an antioxidant (e.g. dioctyl phenylamine, butyl hydroxytoluene, etc.), etc. in an amount within the range conventionaly employed.

EXAMPLES

The present invention will be illustrated in more detail by the following examples. However, it is to be understood that the invention is not intended to be limited by the examples.

In the Examples and Comparative Examples, the samples synthesized in the following Synthesis Examples were used.

Synthesis Example 1

Into a glass reactor, 500 ml of water and 144 g (1 mole) of powdered molybdenum trioxide were suspended, and then 221 g (1.5 moles) of 38 wt %-aqueous sodium hydrogensulfide solution was added to the resulting suspension while stirring under closed conditions, followed by reaction for about 30 min. Subsequently, 260 g of toluene was added to the reaction mixture, and 146 g (1.2 moles) of 30 wt %-aqueous hydrochloric acid solution was further added thereto. After further adding 142 g (1.1 moles) of di-n-butylamine and 84 g (1.1 moles) of carbon disulfide at room temperature, the resulting mixture was stirred at room temperature for 30 minutes and then heated to 95° to 102° C. to be reacted for 4 hours. The resulting reaction product was filtered without slurrying, washed initially with 300 ml of toluene and then with 300 ml of water and dried, thereby obtaining 662 g (95% yield) of a solid reaction product of a compound having the following formula:

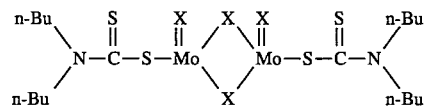

wherein the composition of all Xs was $S_2O_2$.

Subsequently, the solid thus obtained was finely powdered for 2 hours using a mill, whereby a yellow powder (Sample 1) was obtained.

Sample 1 was fractionated by sieving. As a result, a powder composed of particles having diameters of not smaller than 50 μm (Sample 2), a powder composed of particles having diameters of not smaller than 40 μm and smaller than 50 μm (Sample 3) and a powder composed of particles having diameters of smaller than 40 μm (Sample 4) were obtained.

Synthesis Example 2

Into a glass reactor, 300 ml of water and 144 g (1 mole) of powdered molybdenum trioxide were suspended, and then 221 g (1.5 moles) of 38 wt %-aqueous sodium hydrogensulfide solution was added to the resulting suspension while stirring under closed conditions followed by reaction for about 30 min. Subsequently, 260 g of methanol was added to the reaction mixture, and 91 g (0.75 mole) of 30 wt %-aqueous hydrochloric acid solution was further added thereto. After further adding 265 g (1.1 moles) of di-2-ethylhexylamine and 84 g (1.1 moles) of carbon disulfide at room temperature, the resulting mixture was stirred at room temperature for 30 minutes and then heated to 95° to 102° C. to be reacted for 4 hours. The reaction product was present in a methanol-water emulsion as aggigations. The reaction product was filtered without slurrying, washed initially with 300 ml of methanol and then with 300 ml of water and dried, thereby obtaining 648 g (95% yield) of a solid reaction product. Subsequently, the solid thus obtained was finely powdered for 2 hours using a mill, whereby a yellow powder (Sample 5) was obtained.

Sodium content and particle diameters of Samples 1 to 5 given by Synthesis Examples 1 and 2 are summarized in Table 1. In this evaluation of each sample, the sodium content was determined according to the ICP method after ashing the sample, and the particle diameter was determined by laser diffusion using a microtrack particle size distribution analyzer after dispersing the sample in methanol.

TABLE 1

|  | Sample No. | | | | |
| --- | --- | --- | --- | --- | --- |
|  | 1 | 2 | 3 | 4 | 5 |
| Sodium content (ppm) | 650 | 850 | 800 | 560 | 500 |
| Particle size distribution (%) | | | | | |
| not smaller than 50 μm | 18 | 100 |  |  | 16 |
| 40–50 μm | 14 |  | 100 |  | 13 |
| smaller than 40 μm | 68 |  |  | 100 | 71 |
| Average particle diameter (μm) | 28.5 | 66.2 | 44.0 | 14.1 | 26.2 |

Example 1 and Comparative Example 1

Samples 6 to 9 were prepared by using Samples 2 to 4 above in the blending ratio shown in Table 2. Samples 1 to 5 and Samples 6 to 9 thus prepared were tested for dispersibility in grease and the lubrication. The results are summarized in Table 3.

TABLE 2

|  | Sample No. | | | |
| --- | --- | --- | --- | --- |
|  | 6 | 7 | 8 | 9 |
| Blending ratio | | | | |
| Sample 2 |  | 5% | 5% |  |
| Sample 3 | 5% | 10% |  | 10% |
| Sample 4 | 95% | 85% | 95% | 90% |
| Average particle diameter (μm) | 15.6 | 19.7 | 16.7 | 17.1 |

TABLE 3

|  | Sample No. | | | | | | | | |
| --- | --- | --- | --- | --- | --- | --- | --- | --- | --- |
|  | Example 1 | | | | Comparative Example | | | | |
|  | 3 | 4 | 6 | 9 | 1 | 2 | 5 | 7 | 8 |
| Dispersibility in grease test | 29 | 12 | 19 | 25 | 39 | 51 | 32 | 50 | 42 |
| Number of aggregates | | | | | | | | | |
| SRV friction test | | | | | | | | | |
| Friction coefficient (after 30 min.) | 0.098 | 0.085 | 0.092 | 0.095 | 0.105 | 0.105 | 0.104 | 0.105 | 0.104 |
| Amplitude of friction coefficient (after 30 min.) | 0.018 | 0.010 | 0.015 | 0.018 | 0.025 | 0.025 | 0.021 | 0.022 | 0.023 |

Dispersibility in grease test

Into a kneader, 100 parts by weight of a urea grease and 3 parts by weight of each sample were charged, and then mixed at 80° C. for 2 hours. Thereafter, the resulting grease mixture was applied on a glass plate in a thickness of about 1 mm, and then the dispersing state of the sample in the grease mixture was observed by means of a 20× reflection microscope. The dispersibility in grease of each sample was evaluated by counting the number of aggregations of the sample which were present within the 3 mm² on the plate.

Friction test

The friction test was carried out by means of a SRV dynamic friction test machine under the following conditions. The friction properties of each sample were evaluated by reading the coefficient of friction given after 30 minutes and the deflection of the coefficient of friction caused by a slight vibration. In this test, the same grease mixtures were used as those used in the dispersion test above.

Test conditions:
Load: 50N
Temperature: 50° C.
Test time: 60 min.
Amplitude: 1 mm
Frequency of amplitude: 50 times/sec.

Synthesis Example 3

Into a glass reactor, 500 ml of water and 144 g (1 mole) of powdered molybdenum trioxide were suspended, and then 221 g (1.5 moles) of 38 wt %-aqueous sodium hydrogensulfide solution was added to the resulting suspension while stirring under closed conditions and then reacted for about 30 min. Subsequently, 260 g of toluene was added to the reaction mixture, and 146 g (1.2 moles) of 30 wt %-aqueous hydrochloric acid solution was further added thereto. After further adding 142 g (1.1 moles) of di-n-butylamine and 84 g (1.1 moles) of carbon disulfide at room temperature, the resulting mixture was stirred at room temperature for 30 minutes, and then heated to 95° to 102° C. to be reacted for 4 hours. The reaction product was present in a toluene-water emulsion as aggregations. The emulsion containing the reaction product was slurryed by adding 86 g of toluene, and then filtered out. The resultant slurry was washed initially with 300 ml of toluene and then with 300 ml of water and dried, thereby obtaining 648 g (93% yield) of a solid reaction product. Subsequently, the solid thus obtained was finely powdered for 2 hours using a mill, whereby a yellow powder (Sample 10) was obtained. The sodium content and particle size distribution of Sample 10 are shown in Table 4.

In this process, the amount of toluene used for slurrying was 0.6 times by weight that of molybdenum trioxide, and the equivalent number of the mineral acid based on 1 equivalent of the alkali was 0.8.

Synthesis Example 4

Into a glass reactor, 500 ml of water and 144 g (1 mole) of powdered molybdenum trioxide suspended, and then 221 g (1.5 moles) of 38 wt %-aqueous sodium hydrogensulfide solution was added to the resulting suspension while stirring under closed conditions and then reacted for about 30 min. Subsequently, 91 g (0.75 moles) of 30 wt %-aqueous hydrochloric acid solution was further added to the reaction mixture. After further adding 265 g (1.1 moles) of di-2-ethylhexylamine and 84 g (1.1 moles) of carbon disulfide at room temperature, the resulting mixture was stirred at room temperature for 30 minutes, then heated to 95° to 102° C. and reacted for 4 hours. The resulting reaction solution was cooled to 40° C. to aggregate the reaction product, and then 86 g of methanol was added thereto to produce a slurry. The resulting slurry was filtered, washed initially with 300 ml of methanol and then with 300 ml of water and dried, thereby obtaining 857 g (93% yield) of a solid reaction product. Subsequently, the solid thus obtained was finely powdered for 2 hours using a mill, whereby a yellow powder (Sample 11) was obtained. The sodium content and particle size distribution of Sample 11 are also shown in Table 4.

In this process, the amount of methanol used for slurrying was 0.6 times by weight that of molybdenum trioxide, and the equivalent number of the mineral acid based on 1 equivalent of the alkali was 0.5.

TABLE 4

|  | Sample No. | | | | |
| --- | --- | --- | --- | --- | --- |
|  | 10 | 11 | 12 | 13 | 14 |
| Sodium content (ppm) | 20 | 15 | 30 | 14 | 20 |
| Particle size distribution (%) | | | | | |
| not smaller than 50 μm | 0 | 0 | 0 | 0 | 0 |
| 40–50 μm | 0 | 1 | 2 | 0 | 0 |
| smaller than 40 μm | 100 | 99 | 98 | 100 | 100 |
| Average particle diameter (μm) | 6.0 | 10.1 | 13.0 | 7.2 | 8.9 |

As shown in Table 4 above, the two kinds of molybdenum oxysulfide dithiocarbamate produced by Synthesis Examples 3 and 4 had reduced sodium i.e. impurity contents, and comprised fine particles, as they were produced by a process in which a slurrying step was incorporated as described above.

Synthesis Example 5

Into a glass reactor, 200 ml of water and 206 g (1 mole) of powdered ammonium molybdate were suspended, and then 101 g (1.3 moles) of powdered sodium sulfide was added to the resulting suspension while stirring under closed conditions and then reacted for about 1 hour. Subsequently, 400 g of methanol was added to the reaction mixture. After further adding 313 g (1.3 moles) of di-2-ethylhexylamine and 91 g (1.2 moles) of carbon disulfide at room temperature, the resulting mixture was stirred at 60° C. for 1 hour. Thereafter, 120 g (0.4 mole) of 32 wt %-aqueous sulfuric acid solution was further added to the reaction mixture, and the resulting mixture was then heated to 75° to 85° C. and reacted for 4 hours. The resulting reaction solution was cooled to 40° C. to aggregate the reaction product, and then 175 g of methanol was added thereto to give a slurry. The resulting slurry was filtered, washed initially with 400 ml of water and then with 400 ml of methanol and dried, thereby obtaining 820 g (89% yield) of a solid reaction product. Subsequently, the solid thus obtained was finely powdered for 2 hours using a mill, whereby a yellow powder (Sample 12) was obtained. The sodium content and particle size distribution of Sample 12 are also shown in Table 4.

In this process, the amount of methanol used for slurrying was 0.85 times by weight that of molybdenum trioxide, and the equivalent number of the mineral acid based on 1 equivalent of the alkali was 0.3.

Synthesis Example 6

Into a glass reactor, 200 ml of water and 144 g (1 mole) of powdered molybdenum trioxide were suspended, and then 117 g (1.5 moles) of powdered sodium sulfide was added to the resulting suspension while stirring under closed conditions and then reacted for about 30 min. Subsequently, 260 g of methanol was added to the reaction mixture, and then 255 g (2.1 moles) of 30 wt %-aqueous hydrochloric acid solution was added thereto. After further adding 168 g (1.3 moles) of di-isobutylamine and 99 g (1.3 moles) of carbon disulfide at room temperature, the resulting mixture was stirred at room temperature for 30 minutes, and then heated to 75° to 85° C. to be reacted for 4 hours. The reaction product was present in a methanol-water solution as aggregations. The solution containing the reaction product was slurryed by adding 288 g of toluene, and then filtered. The resultant slurry was washed initially with 300 ml of toluene and then with 300 ml of water and dried, thereby obtaining 592 g (85% yield) of a solid reaction product. Subsequently, the solid thus obtained was finely powdered for 2 hours using a mill, whereby a yellow powder (Sample 13) was obtained. The sodium content and particle size distribution of Sample 13 are shown in Table 4.

In this process, the amount of toluene used for slurrying was 2 times by weight that of molybdenum trioxide, and the equivalent number of the mineral acid based on 1 equivalent of the alkali was 0.7.

Synthesis Example 7 (Comparative Example)

Into a glass reactor, 500 ml of water and 144 g (1 mole) of powdered molybdenum trioxide were suspended, and then 221 g (1.5 moles) of 38 wt %-aqueous sodium hydrogensulfide solution was added to the resulting suspension while stirring under closed conditions and then reacted for about 30 minutes. Subsequently, 260 g of methanol and 255 g (2.1 moles) of 30 wt %-aqueous hydrochloric acid solution were added to the reaction mixture. After further adding 265 g (1.1 moles) of di-2-ethylhexylamine and 84 g (1.1 moles) of carbon disulfide at room temperature, the resulting mixture was stirred at room temperature for 30 minutes. Thereafter, the resulting mixture was then heated to 95° to 102° C. and reacted for 4 hours. The resulting reaction solution was cooled to 40° C. to aggregate the reaction product, and then 86 g of methanol was added thereto to produce a slurry. The resulting slurry was filtered, washed initially with 300 ml of methanol and then with 300 ml of water and dried, to obtain 903 g (98% yield) of a black solid reaction product. As the resulting solid contained a large amount of impurities, the solid was separated out on a chromatographic column to obtain 230 g (25% yield) of a yellow reaction product.

In this process, the amount of methanol used for slurrying was 0.6 times by weight that of molybdenum trioxide, and the equivalent number of the mineral acid based on 1 equivalent of the alkali was 1.4.

Synthesis Example 8 (Comparative Example)

Into a glass reactor, 500 ml of water and 144 g (1 mole) of powdered molybdenum trioxide were suspended, and then 221 g (1.5 moles) of 38 wt %-aqueous sodium hydrogensulfide solution was added to the resulting suspension while stirring under closed conditions and was reacted for about 30 minutes. Subsequently, 260 g of toluene and then 36 g (0.3 moles) of 30 wt %-aqueous hydrochloric acid solution were added to the reaction mixture. After further adding 142 g (1.1 moles) of di-n-butylamine and 84 g (1.1 moles) of carbon disulfide at room temperature, the resulting mixture was stirred at room temperature for 30 min. Thereafter, the resulting mixture was heated to 95° to 102° C. and reacted for 4 hours. The reaction product was present in a toluene-water emulsion as aggregates. Said emulsion containing the reaction product was slurried by adding 86 g of toluene, and then filtered. The resultant product was washed initially with 300 ml of toluene and then with 300 ml of water and dried, thereby obtaining 140 g (20% yield) of a solid reaction product. Subsequently, the solid thus given was finely powdered for 2 hours using a mill, whereby a yellow powder was obtained.

In this process, the amount of toluene used for slurrying was 0.6 times by weight that of molybdenum trioxide, and the equivalent number of the mineral acid based on 1 equivalent of the alkali was 0.2.

Synthesis Example 9

The same procedures as Synthesis Example 4 were carried out except that di-n-octylamine (1.1 moles) was used instead of di-2-ethylhexylamine (1.1 moles). The sample obtained by this process is referred to as Sample 14. The sodium content and particle size distribution of Sample 14 are also shown in Table 4.

Example 2

Dispersibility in grease tests and the lubrication tests were carried out on Sample 10 to 14. The results are summarized in Table 5.

Friction test

The friction test was carried out by means of a SRV dynamic friction test machine under the following conditions. The friction property of each sample was evaluated by reading the coefficient of friction given after 30 minutes and the deflection of the coefficient of friction caused by a slight vibration. In this test, the same grease mixtures were used as those used in the dispersion test above.

Test conditions:
 Load: 50N
 Temperature: 50° C.
 Test time: 60 min.
 Amplitude: 1 mm
 Frequency of amplitude: 50 times/sec.

As described above, an effect of the present invention is that a powdery molybdenum oxysulfide dithiocarbamate composition can be provided which, when used for a grease composition, exhibits excellent wear and abrasive properties and, therefore, exhibits excellent lubricating properties, as well as decreased corrosive action.

Another effect of the present invention is that a process for effective production of the powdery molybdenum oxysulfide dithiocarbamate composition described above may be provided.

A further effect of the present invention is that a grease composition which exhibits excellent wear and abrasive properties and, therefore, exhibits excellent lubricating properties, as well as decreased corrosive action can be provided. That is, the grease composition of the present invention, which comprises a molybdenum oxysulfide dithiocarbamate composition having ready dispersibility in a base grease, can exhibit excellent friction and abrasive properties and decreased corrosive action in a lubrication system, and therefore, can be used as a grease for all purposes such as in synchronized joints of automobiles.

What is claimed is:

1. A process for production of a powdered molybdenum oxysulfide dithiocarbamate composition comprising a compound represented by the following formula (I):

TABLE 5

| | Example 2 Blending Sample No. | | | | | | |
|---|---|---|---|---|---|---|---|
| | 10 | 10 | 10 | 11 | 12 | 13 | 14 |
| Blending amount (%) | 1 | 3 | 5 | 3 | 3 | 3 | 3 |
| Dispersibility in grease test Number of aggregates | 4 | 8 | 10 | 4 | 10 | 5 | 8 |
| SVR friction test | | | | | | | |
| Friction coefficient (after 30 min.) | 0.095 | 0.075 | 0.085 | 0.065 | 0.074 | 0.068 | 0.073 |
| Amplitude of friction coefficient (after 30 min.) | 0.015 | 0.008 | 0.012 | 0.004 | 0.010 | 0.006 | 0.009 |

Dispersibility in grease test

Into a kneader, 100 parts by weight of a urea grease and 3 parts by weight of each sample were charged, and then mixed at 80% for 2 hours. Thereafter, the resulting grease mixture was applied on a glass plate in a thickness of about 1 mm, and then the dispersing state of the sample in the grease mixture was observed by means of a 20× reflection microscope. The dispersibility in grease of each sample was evaluated by counting the number of aggregations of the sample which were present within the 3 mm² on the plate.

$$\begin{array}{c} R^1 \\ \diagdown \\ R^2 \diagup \end{array} N - \overset{S}{\underset{\|}{C}} - S - Mo \overset{X}{\underset{X}{\diagdown}} \overset{X}{\diagup} Mo - S - \overset{S}{\underset{\|}{C}} - N \begin{array}{c} \diagup R^3 \\ \diagdown R^4 \end{array}$$

wherein $R^1$, $R^2$, $R^3$ and $R^4$ are independent hydrocarbyl groups and may be the same or different groups, and wherein the total number of carbon atoms of $R^1$ to $R^4$ is 4 to 36; and X is sulfur or oxygen and the composition of the total of all Xs is represented by $S_m$ and $O_n$ in which m and n satisfy the ranges of $1.7 \leq m \leq 3.5$ and $0.5 \leq n \leq 2.3$, respectively, and in which the constituent particles have diameters of not larger than 50 μm, comprising:

reacting (a) molybdenum trioxide or an alkali metal salt or an ammonium salt of molybdic acid with (b) alkali hydrogen sulfide or alkali sulfide in a molar ratio of (a):(b)=1:1 to 1:2 in an aqueous medium, thereby preparing an aqueous solution or suspension (A) of a reaction product;

reacting said reaction product (A) with (B) carbon disulfide, (C) secondary amine, and (D) a mineral acid in amounts such that the molar ratio of (A), (B) and (C) is (A):(B):(C)=1:0.9–2:0.9–2 and the amount of (D) reacted satisfies the expression: $1-[(R'/r)+1] \times 1/10 \leq d \leq 1$, wherein R' is the total number of carbon atoms present in $R^1$, $R^2$, $R^3$ and $R^4$ in the formula of the molybdenum oxysulfide dithiocarbamate compound above and d is the equivalent number of the mineral acid versus the alkali present in reaction product (A) when the alkali equivalent in reaction product (A) is defined as 1;

separating the solid reaction product prepared from the solution or suspension;

slurring the resulting reaction product in an organic solvent; and then, after separating the separated solid molybdenum oxysulfide dithiocarbamate product, washing, drying and powdering the solid product.

2. The process according to claim 1, wherein the alkali metal salt of molybdic acid is sodium molybdate and/or potassium molybdate and the ammonium salt of molybdic acid is ammonium molybdate.

3. The process according to claim 1, wherein the alkali hydrogensulfide is sodium hydrogensulfide and/or potassium hydrogensulfide.

4. The process according to claim 1, wherein the alkali sulfide is sodium sulfide, potassium sulfide and/or ammonium sulfide.

5. The process according to claim 1, wherein the secondary amine is one having a hydrocarbyl substituent group.

6. The process according to claim 5, wherein the hydrocarbyl substituent group is one selected from the group consisting of ethyl, propyl, isopropyl, butyl, isobutyl, pentyl, hexyl, heptyl, octyl and 2-ethylhexyl.

7. The process according to claim 1, wherein the reaction between the components (A), (B), (C) and (D) is carried out at room temperature or under added heated conditions.

8. The process according to claim 7, wherein the heated conditions are within the temperature range of 60° to 110° C.

9. The process according to claim 1, wherein the organic solvent is a volatile aromatic, aliphatic or aliphatic-aromatic organic compound.

10. The process according to claim 9, wherein the organic solvent is one selected from the group consisting of methanol, ethanol, 2-propanol, benzene, toluene and xylene.

11. A grease composition comprising: 0.1 to 10 parts by weight of a powdered molybdenum oxysulfide dithiocarbamate composition which comprises a compound represented by the following formula:

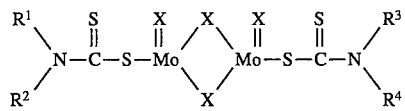

wherein $R^1$, $R^2$, $R^3$ and $R^4$ are independent hydrocarbyl groups and may be the same or different groups, and the total number of carbon atoms contained in $R^1$ to $R^4$ is 4 to 36; and wherein X is sulfur or oxygen and the composition of the total of all Xs is given as $S_m$ and $O_n$ in which m and n satisfy the ranges of $1.7 \leq m \leq 3.5$ and $0.5 \leq n \leq 2.3$, respectively, prepared by the process of claim 1, in which the constituent particles have diameters of not larger than 50 μm, based on 100 parts by weight of a base grease.

12. The grease composition of claim 11, wherein the constituent particles are composed of not more than 5% by weight of particles having diameters of 40 to 50 μm and of not less than 95% by weight of particles having diameters of smaller than 40 μm based on the total weight of the composition.

13. The grease composition of claim 12, wherein the constituent particles have an average diameter of not larger than 20 μm.

* * * * *